United States Patent
Porter et al.

(10) Patent No.: US 9,226,739 B2
(45) Date of Patent: Jan. 5, 2016

(54) BIORESORBABLE DETACHABLE TIP DESIGN FOR ADHESIVE-BASED EXTRAVASCULAR CLOSURE DEVICE

(71) Applicant: St. Jude Medical Puerto Rico LLC, Caguas, PR (US)

(72) Inventors: Deanna Porter, Woodbury, MN (US); Zhengrong Zhou, Shanghai (CN)

(73) Assignee: ST. JUDE MEDICAL PUERTO RICO LLC, Caguas, PR (US)

( * ) Notice: Subject to any disclaimer, the term of this patent is extended or adjusted under 35 U.S.C. 154(b) by 346 days.

(21) Appl. No.: 13/771,912

(22) Filed: Feb. 20, 2013

(65) Prior Publication Data

US 2014/0236223 A1 Aug. 21, 2014

(51) Int. Cl.
| | |
|---|---|
| *A61B 17/08* | (2006.01) |
| *A61D 1/00* | (2006.01) |
| *A61B 17/00* | (2006.01) |
| *A61B 17/22* | (2006.01) |
| *A61B 17/04* | (2006.01) |

(52) U.S. Cl.
CPC ....... *A61B 17/0057* (2013.01); *A61B 17/00491* (2013.01); *A61B 2017/00004* (2013.01); *A61B 2017/0065* (2013.01); *A61B 2017/00623* (2013.01); *A61B 2017/00654* (2013.01); *A61B 2017/00659* (2013.01); *A61B 2017/0406* (2013.01); *A61B 2017/22067* (2013.01)

(58) Field of Classification Search
CPC .................. A61B 17/0057; A61B 2017/0065; A61B 2017/00672
USPC ................................................ 606/213, 214
See application file for complete search history.

(56) References Cited

U.S. PATENT DOCUMENTS

| | | | | |
|---|---|---|---|---|
| 5,192,302 | A | * | 3/1993 | Kensey et al. ................ 606/213 |
| 5,350,399 | A | * | 9/1994 | Erlebacher et al. ........... 606/213 |
| 2006/0047313 | A1 | | 3/2006 | Khanna et al. |
| 2006/0173492 | A1 | * | 8/2006 | Akerfeldt et al. ............. 606/232 |
| 2009/0088793 | A1 | * | 4/2009 | Bagaoisan et al. ............ 606/213 |
| 2010/0211000 | A1 | * | 8/2010 | Killion et al. .................... 604/57 |
| 2012/0143249 | A1 | * | 6/2012 | Jenson et al. ................. 606/232 |
| 2012/0245517 | A1 | | 9/2012 | Tegels |
| 2013/0190813 | A1 | | 7/2013 | Tegels et al. |

FOREIGN PATENT DOCUMENTS

| | | |
|---|---|---|
| WO | 2012148745 A1 | 11/2012 |
| WO | 2013112340 A1 | 8/2013 |

OTHER PUBLICATIONS

PCT International Search Report for PCT International No. PCT/US2013/069596, mailed Feb. 4, 2015 (5 pp.).

* cited by examiner

*Primary Examiner* — Katherine M Shi
(74) *Attorney, Agent, or Firm* — Holland & Hart (57) ABSTRACT

A vascular closure device includes a vessel locating device, a sealant delivery device, a detachable sealing tip, and a suture. The vessel locating device includes an expandable portion configured to extend through and temporarily seal a vessel puncture from within a vessel. The sealant delivery device is configured to deliver a first volume of flowable sealant to the vessel puncture along an exterior of the vessel. The detachable sealing tip is carried at a distal end of the vessel locating device. The suture is connected to and extends proximally from the detachable sealing tip. The detachable sealing tip is configured for release within the first volume of flowable sealant upon withdrawal of the vessel locating device through the first volume of flowable sealant. The suture is anchored at a location proximal of the detachable sealing tip.

16 Claims, 13 Drawing Sheets

BIORESORBABLE DETACHABLE TIP DESIGN FOR ADHESIVE-BASED EXTRAVASCULAR CLOSURE DEVICE

TECHNICAL FIELD

The present disclosure relates generally to methods and systems for sealing tissue punctures, and more particularly, to methods and systems for depositing and securing a secondary sealing member to seal tissue punctures.

BACKGROUND

Various surgical procedures are routinely carried out intravascularly or intraluminally. For example, in the treatment of vascular disease, such as arteriosclerosis, it is a common practice to access the artery and insert an instrument (e.g., a balloon or other type of catheter) to carry out a procedure within the artery. Such procedures usually involve the percutaneous puncture of the artery so that an insertion sheath may be placed in the artery and thereafter instruments (e.g., catheters) may pass through the sheath to an operative position within the artery. Intravascular and intraluminal procedures unavoidably present the problem of stopping the bleeding at the percutaneous puncture after the procedure has been completed and after the instruments (and any insertion sheaths used therewith) have been removed. Bleeding from puncture sites, particularly in the case of femoral arterial punctures, is typically stopped by utilizing vascular closure devices.

While there are a variety of prior art devices and techniques for closing such punctures, one method includes temporarily sealing the tissue puncture intravascularly using an inflation balloon. A sealing material may be delivered to an outer surface of the tissue to seal the tissue puncture while maintaining the temporary seal from the balloon. Removing the collapsed balloon through the sealing material may leave a channel through the sealing material that poses a potential lack of hemostasis. The channel through the sealing material may be closed by depositing a detachable tip in the tract. Opportunities exist for improvements in detachable tip constructions and methods of placement.

SUMMARY

One aspect of the present disclosure relates to a vascular closure device, which includes a vessel locating device, a sealant delivery device, a detachable sealing tip, and a suture. The vessel locating device includes an expandable portion configured to extend through and temporarily seal a vessel puncture from within a vessel. The sealant delivery device is configured to deliver a first volume of flowable sealant to the vessel puncture at an exterior surface of the vessel. The detachable sealing tip is carried at a distal end of the vessel locating device. The suture is connected to and extends proximally from the detachable sealing tip. The detachable sealing tip is configured for release within the first volume of flowable sealant upon withdrawal of the vessel locating device through the first volume of flowable sealant. The suture is anchored proximal of the detachable sealing tip.

The suture may be connected to a distal end of the detachable sealing tip. The suture may be connected to a proximal end of the detachable sealing tip. The detachable sealing tip includes an elongate cylindrical shape. The detachable sealing tip may include a mesh material. The suture may wrap around the detachable sealing tip. The suture may be connected to a securement member, which contacts an outer skin surface of the patient.

The suture and detachable sealing tip may each include a bioresorbable material, wherein the bioresorbable material of the detachable sealing tip has a faster rate of resorption than a material of the suture. The detachable sealing tip may include a lumen extending between distal and proximal ends of the detachable sealing tip, and the suture extends through the lumen. At least a portion of the detachable sealing tip may be positioned within the vessel locating device prior to being detached within the first volume of flowable sealant. The sealant delivery device may include first and second lumens, the first volume of flowable sealant is delivered through the first lumen, and the vessel locating device extends through the second lumen.

Another aspect of the present disclosure relates to a vascular closure device for sealing a vessel puncture of a patient. The vascular closure device includes a sealant delivery device and a detachable sealing tip assembly. The sealant delivery device is configured to deposit a volume of flowable sealant adjacent to a vessel puncture. The detachable sealing tip assembly is configured to seal a channel formed in the volume of flowable sealant upon removal of the vascular closure device from the patient. The detachable sealing tip assembly includes a carrier tube, a sealing tip positioned at a distal end of the carrier tube, a suture having a distal end releasably connected to the sealing tip and a proximal end extending outside of the patient, and a securement device connected to the proximal end of the suture and configured to anchor the sealing tip against an outer skin surface of the patient after the sealing tip is released from the carrier tube within the channel.

The suture may fix the sealing tip relative to the carrier tube until the sealing tip is released in the channel. The securement device may be connected to the suture after removal of the vascular closure device from the patient. The vascular closure device may include an expandable balloon mounted to the carrier tube at a location proximal of the sealing tip. The expandable balloon may be operable to temporarily seal the vessel puncture during delivery of the volume of flowable sealant. At least a portion of the sealing tip may be earned within a distal end portion of the earner tube.

Another aspect of the present disclosure relates to a method of sealing a vessel puncture in a patient. The method includes providing a vascular closure device having a sealant delivery device, a sealing tip, and a suture connected to the sealing tip. The method also includes advancing the vascular closure device to the vessel puncture, and delivering a volume of flowable sealant to the vessel puncture with the sealant delivery device. The method further includes withdrawing a portion of the vascular closure device through the volume of flowable sealant to define a channel in the volume of flowable sealant, releasing the sealing tip in the channel, extending the suture proximally from the sealing tip, and connecting the suture to the patient.

The method may also include providing a suture securement device, and connecting the suture securement device to the suture to anchor the sealing tip against an outer skin surface of the patient. The suture and suture securement device may retain the sealing tip from moving distally through the vessel puncture. The method may include retaining the sealing tip to the vascular closure device with the suture prior to releasing the sealing tip in the channel. Connecting the suture securement device to the suture may include inserting the suture through the suture securement device and advancing the suture securement device along the suture to the outer skin surface.

The vascular closure device may include a vessel locating member positioned proximal of the sealing tip, and the method includes inserting the vessel locating member through the vessel puncture and expanding the vessel locating member to temporarily seal the vessel puncture while delivering the volume of flowable sealant to the vessel puncture. The method may include delivering another volume of flowable sealant to the channel after releasing the sealing tip in the channel.

The foregoing and other features, utilities, and advantages of the invention will be apparent from the following detailed description of the invention with reference to the accompanying drawings.

BRIEF DESCRIPTION OF THE DRAWINGS

The accompanying drawings illustrate various embodiments of the present disclosure and are a part of the specification. The illustrated embodiments are merely examples of the present disclosure and do not limit the scope of the invention.

Throughout the drawings, identical reference numbers designate similar, but not necessarily identical, elements.

DETAILED DESCRIPTION

The systems and methods disclosed herein may be used to close or seal percutaneous punctures made through the body tissue of a patient to gain access to a body cavity of a patient. Access through these percutaneous punctures allows a physician to carry out various procedures in or through the body cavity for examination, surgery, treatment and the like. While not meant to be limiting, the systems are illustrated being used to seal percutaneous punctures that provide access to blood vessels in patients for various procedures. It will be appreciated that the systems are applicable to other procedures requiring sealing of a puncture through body tissue into a cavity including, for example, laparoscopic surgery and other microscopic surgery techniques using a relatively small incision.

The general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

As used in this specification and the appended claims, the terms "engage" and "engageable" are used broadly to mean interlock, mesh, or contact between two structures or devices. Likewise "disengage" or "disengageable" means to remove or capable of being removed from interlock, mesh or contact. A "tube" is an elongated device with a passageway. The passageway may be enclosed or open (e.g., a trough). A "lumen" refers to any open space or cavity in a bodily organ, especially in a blood vessel. The words "including" and "having," as wed as their derivatives, as used in the specification, including the claims, have the same meaning as the word "comprising."

An example embodiment of the present disclosure includes a vascular closure device having a detachable sealing tip. The vascular closure device is used with a sheath that provides access through a vessel puncture and into an inner lumen of the vessel. The vascular closure device operates to release a detachable sealing plug (e.g., sealing tip) from a distal end of the vascular closure device after deployment of a flowable sealant at the vessel puncture. The vascular closure device may include a sealant delivery device and a vessel locating device (also referred to as a temporary sealing device) such as a balloon location device. The locating device is inserted through the vessel puncture, expanded and anchored against an internal surface of the vessel adjacent to the vessel puncture. The sealant delivery device deposits a volume of flowable sealant along an external surface of the vessel adjacent to the vessel puncture. After the sealant is deposited and cured, the location device is withdrawn through the sealant, which leaves an opening or channel through the sealant. The channel may be sealed by locating and releasing the sealing tip within the channel. The sealing tip may be carried at the distal end of the vascular closure device to improve ease of positioning the sealing tip within the channel.

The sealing tip may be secured at the distal end of the location device using an elongated connection member such as, for example, a filament (e.g., a wire or suture) or other linkage that extends along a length of the vascular closure device from the sealing tip at a distal end of the location device to a proximal end of the vascular closure device. The sealing tip is released from the distal end of the location device by releasing the connection member at the proximal end of the vascular closure device. In one example, the connection member is released by operating an actuation member such as a lever or other feature. The actuation member may be carried by a housing or handle at a proximal end portion of the vascular closure device. Releasing the connection member at the proximal end allows the sealing tip to release from the distal end of the location device. The connection member is typically held under tension to retain the sealing tip at a distal end portion of the vascular closure device until the sealing tip is properly positioned within the deposited volume of sealing material.

The connection member may be released in a number of ways, such as, for example, breaking the connection member using a tension force or cutting the connection member at any location along a length of the location device. In another example, a knot or other connection feature used to secure the connection member to the location device may be released to disconnect the connection member from an anchor feature such as, for example, the housing. The actuation member mention above may be used to release the connection member from the vascular closure device.

The examples disclosed herein may provide an improved design for a bioresorbable sealing tip (e.g., a detachable sealing tip or detachable plug), which is one of the sealing components used for an adhesive-based extravascular closure device. The new detachable tip design may combine at least some of the advantages and address at least some of the disadvantages of existing designs, and is intended to enhance in vivo device safety and minimize device profile while maintaining performance. The detachable tip may provide an immediate and secure vascular hemostasis regardless of, for example, anticoagulation status of the deposited bioadhesive, the presence of peripheral vascular disease, and low-stick location.

The example vascular close device as disclosed herein may implement a delivery system to position a flowable resorbable bioadhesive and a resorbable detachable tip at the site of a vessel puncture to provide immediate and secure hemostasis. The vessel puncture is typically in the range of about 5 F to about 20 F. Vessel punctures in the range of greater than 10 F may be classified as "large bore" vessel punctures. The vascular closure device may include a balloon location device to temporarily seal the vessel puncture from within the vessel during delivery of a first treatment of bioadhesive (e.g., sealing material) to the vessel puncture site. The bioadhesive may cure within a time frame of about 5 seconds to about 60 seconds, and more specifically, in the range about 5 seconds to about 10 seconds. After the bioadhesive is at least partially cured, the balloon may be deflated and removed from the vessel. A channel is formed through the bioadhesive upon withdrawal of the balloon location device. The detachable tip may be deployed in the channel as the balloon location device is removed through the bioadhesive. The detachable tip may provide temporary field control (i.e., flow through the channel) until, for example, a second treatment of bioadhesive or other means of closing the channel and tissue tract leading to the vessel puncture is positioned. In the case of using a second treatment of bioadhesive, the detachable tip may be locked in place within the channel using the second treatment of bioadhesive. The second treatment of bioadhesive may reinforce the initial or first delivery of bioadhesive.

Typically, the detachable tip provides a temporary seal with the bioadhesive channel, which may be helpful in limiting blood flow from entering the tissue tract. The detachable tip may also limit passage of a secondary injection of bioadhesive from entering the vessel through the vessel puncture. The detachable tip may comprise a bioresorbable material comprising, for example, any of the many known bioresorbable implant materials. Preferably, the detachable tip is as small as possible while still having a size sufficient to at least temporarily plug the channel through the first injection of bioadhesive. The detachable tip preferably includes tip attachment and separation features that provide a relatively safe, reliable and repeatable closure of the channel.

The detachable sealing tip of the present disclosure may comprise both a detachable tip and a connection member such as a filament (e.g., suture) attached to the sealing tip. The suture may be configured to extend through at least a portion of the tissue tract, and may specifically extend to a location outside of the patient. An optional skin securement feature may be used to connect and anchor the suture to the outside of the patient (e.g., against the outer skin surface of the patient). The suture extends proximally from the sealing tip and may be secured to the bioadhesive, which has been deposited within the tissue tract adjacent to the vessel puncture. The bioadhesive may provide anchoring of the sealing tip to limit distal movement of the sealing tip. When using the skin securement feature, the sealing tip may be additionally anchored via the suture and skin securement feature outside of the patient.

The detachable sealing tip of the present disclosure (e.g., including the suture and optional skin securement feature) may limit the possibility of the detachable tip slipping into the vessel and causing potential emboli risk to the patient during or after the second bioadhesive injection, as well as during resorption of the bioadhesive. Resorption of the bioadhesive may occur within about 30 days to about 90 days.

The detachable sealing tip and suture may comprise a bioresorbable material. The materials for the sealing tip may comprise, for example, crystalline/amorphous solid polymers or porous mesh structures (e.g., polyglycolide acid (PGA), polylactic acid (PLA), or poly lactic-co-glycolic acid (PLGA)). The suture may comprise, for example, commercially available PGA, PLA or PLGA. The resorption rate of the suture material may be slower than the resorption rate of the detachable sealing tip and bioadhesive materials. The readily available materials recommended for the sealing tip and suture include, for example, a PLGA sealing tip and a PGA coated suture.

The sealing tip may be carried at a location at least partially spaced distal of a distal most end of the balloon location device. In other arrangements, at least a portion of the sealing tip is positioned within the balloon location device or otherwise within the vascular closure device during delivery. In the case of a sealing tip that comprises a mesh material, the mesh may be compacted and inserted within a cavity at a distal end of the balloon device and later ejected from the cavity for deposit within the channel formed in the bioadhesive.

A suture release mechanism may be integrated into the vascular closure device. The suture release mechanism may comprise, for example, a low force, controlled tip release, which is operable after the balloon is deflated and removed from the vessel. The suture, which is tethered proximally from the sealing tip, may be embedded within, for example, the second injection of bioadhesive upon curing to achieve immediate securement. As discussed above, the suture may optionally be connected to a skin securement device, which is positioned at least partially outside of the patient and may contact an outer skin surface adjacent to the tissue tract leading to the vessel puncture. In at least some examples, the skin securement device may be used in place of the second ejection of bioadhesive to anchor the sealing tip.

Figure 1:
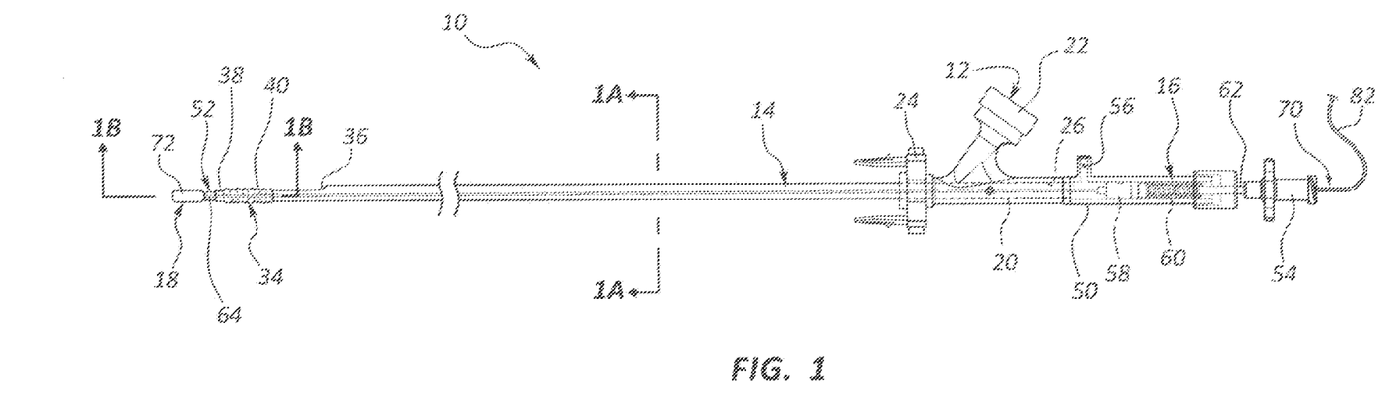
FIG. 1 is a side view of an example vascular closure device in accordance with the present disclosure.
Figure 2:
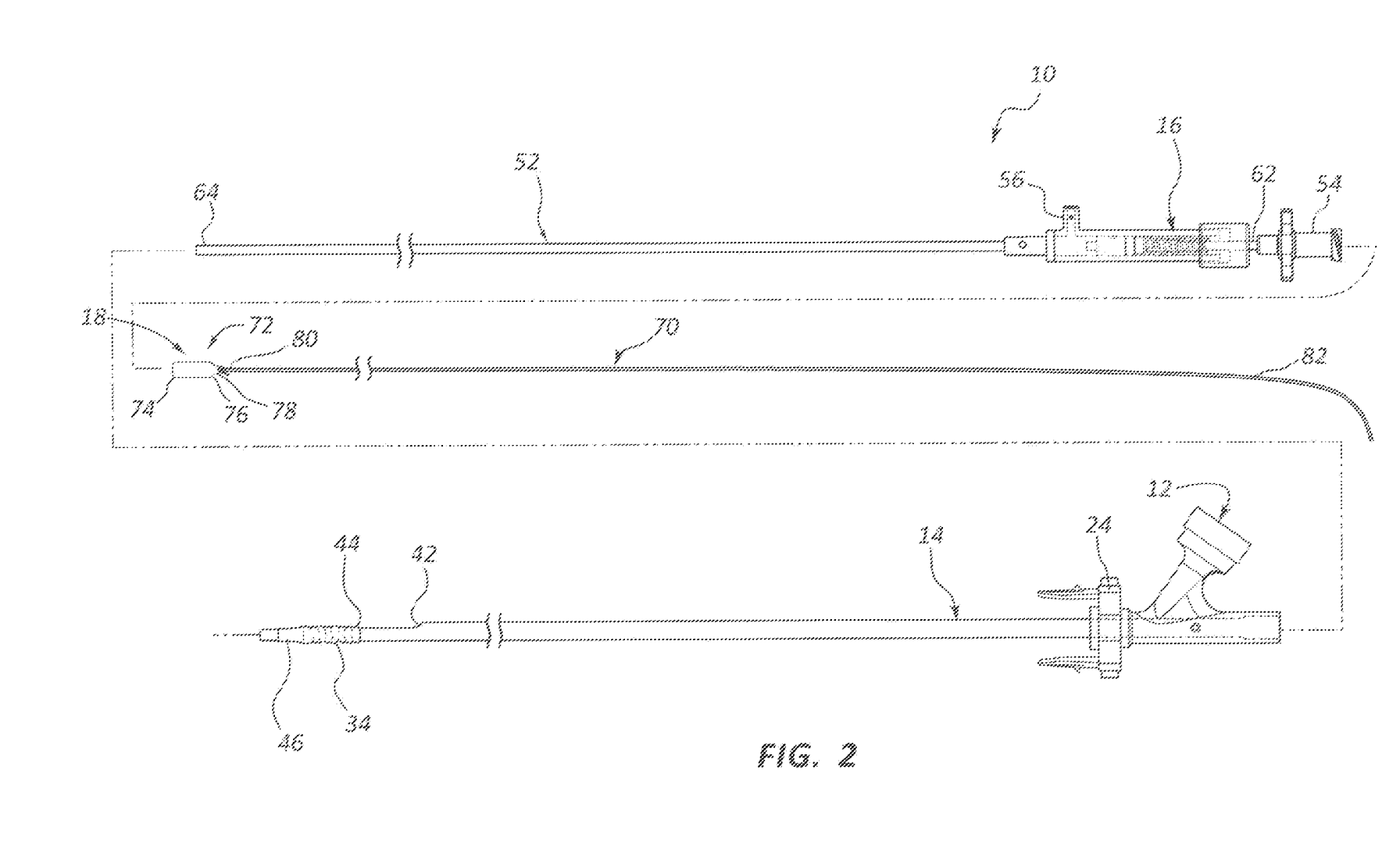
FIG. 2 is an exploded view of the vascular closure device of FIG. 1.

Referring now to FIGS. 1-2, an example vascular closure device 10 is shown including a manifold 12, a delivery tube 14, a balloon location device 16, and a detachable sealing tip assembly 18. FIG. 2 shows the vascular closure device 10 at least partially exploded to separate the manifold 12 and delivery tube 14 from the balloon location device 16 and the detachable sealing tip assembly 18. A suture of the detachable sealing tip assembly 18 extends through the balloon location device 16. A sealing tip of the detachable sealing tip assembly 18 is positioned at a distal end of the balloon location device 16 when assembled. The balloon location device 16 is positioned extending through the manifold 12 and delivery tube 14 and may be positioned at a distal most point on the vascular closure device 10.

The manifold 12 includes a delivery device passage 20, an injection port 22, and a latch 24. The delivery device passage 20 includes a proximal seat 26. A portion of the balloon location device 16 extends into and seats within the delivery device passage 20 against proximal seat 26. The injection port 22 is configured to receive a volume of bioadhesive, which may be carried by, for example, a syringe as shown FIGS. 3-6. The latch 24 is configured to connect to a sheath, such as sheath 2 shown in FIGS. 3-6. The latch 24 provides connection of the vascular closure device 10 to the sheath to provide a fixed spacing between a distal most end of the sheath 2 and a balloon 34 of the balloon location device 16.

Figure 1A:
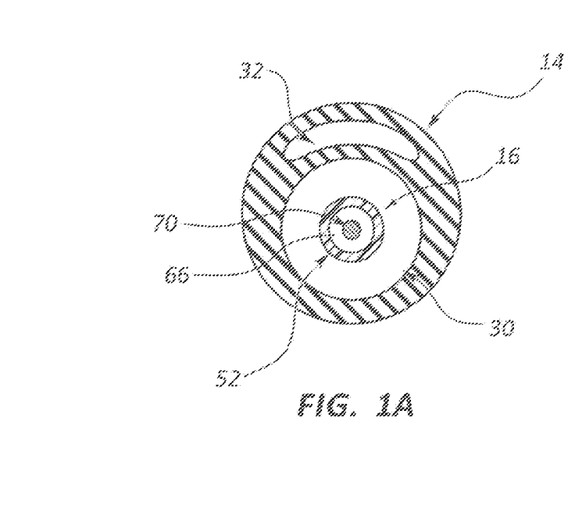
FIG. 1A is a cross-sectional view of the vascular closure device of FIG. 1 taken along cross-section indicators 1A-1A.

The delivery tube 14 includes a first lumen 30, a second lumen 32, and the balloon 34. The second lumen 32 terminates at a distal opening 36. The second lumen 32 is coupled in flow (e.g., fluid) communication with the injection port 22 for delivery of bioadhesive to the vessel puncture. The first lumen 30 receives the balloon location device 16 as shown in FIG. 1A. A space between the balloon location device 16 and a surface that defines the first lumen 30 provides a passage for delivery of inflation fluid to the balloon 34. The balloon 34 may include distal and proximal waists 38, 40. In some arrangements, the proximal waist 40 is connected to an outer surface of the delivery tube 14, and the distal waist 38 is connected to a portion of the balloon location device 16. In some embodiments, the balloon 34 is considered part of the balloon location device 16 rather than part of the delivery tube 14.

Figure 10:
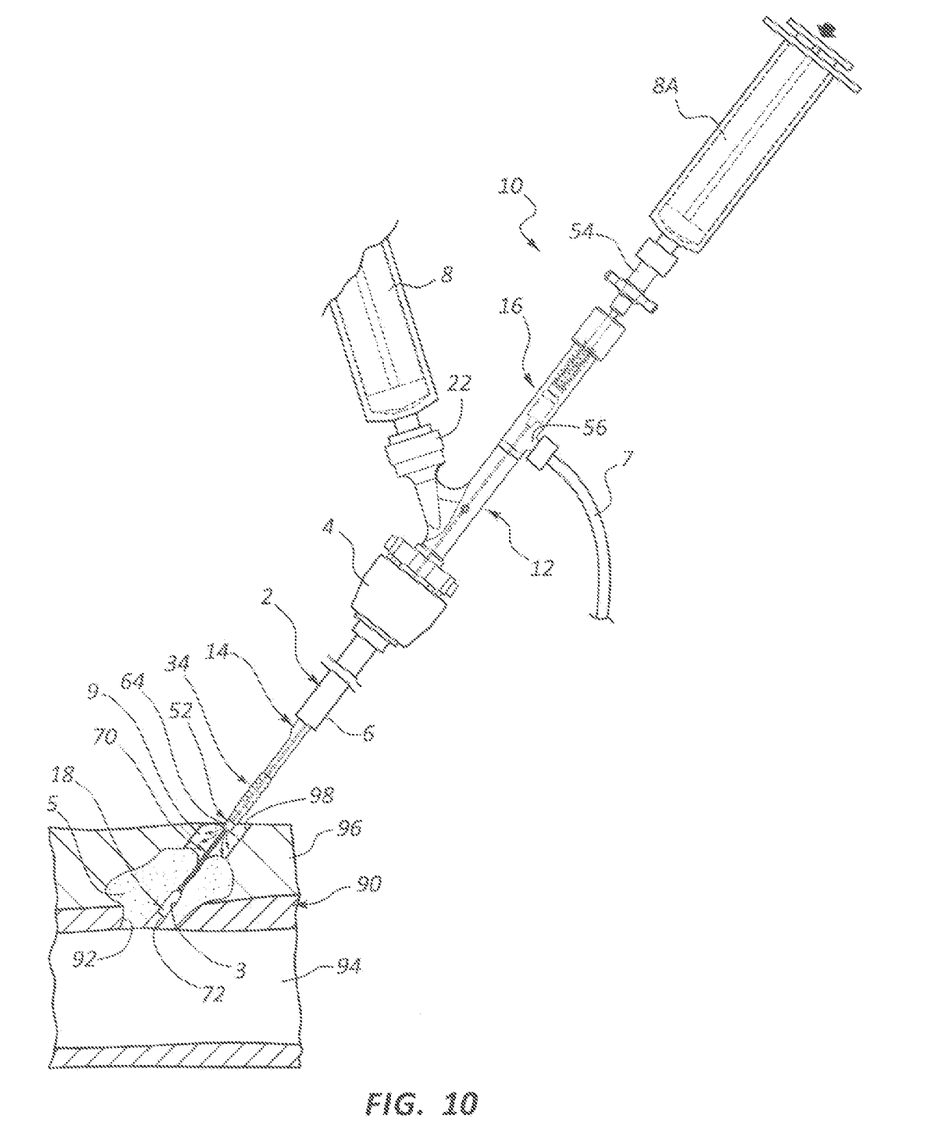

The balloon location device 16 comprises a housing 50, an inner tube 52, an inner tube manifold 54, an inflation manifold 56, a piston 58, and a biasing member 60. The piston 58 and biasing member 60 may be positioned within the housing 50 and provide a visual indicator of, for example, an inflated state of the balloon 34 as described in U.S. Patent Application Ser. No. 61/590,000, filed on 24 Jan. 2012 and entitled "Balloon Location Device Manifold for Vascular Closure Device and Methods," which patent application is incorporated herein in its entirety by this reference. The inner tube 52 may include proximal and distal ends 62, 64 and define a lumen 66. The inner tube manifold 54 may be positioned at the proximal end 62 and provide attachment to, for example, a secondary source of bioadhesive as shown in FIG. 10. In one example, the distal waist 38 of the balloon 34 is connected at the distal end 64 of the inner tube 52.

The inflation manifold 56 may be connected to a source of inflation fluid 7 as shown in FIGS. 3-6. The inflation manifold 56 may be coupled in flow of communication with the first lumen 30 of the delivery tube 14.

Figure 1B:
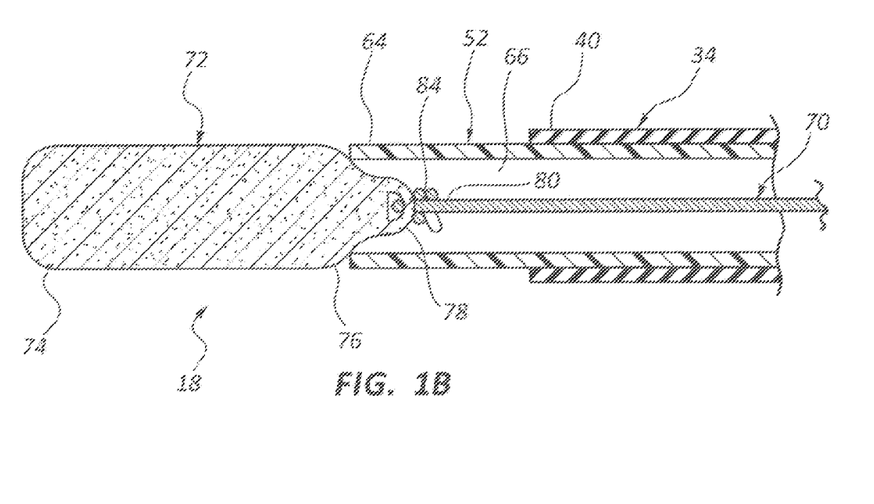
FIG. 1B is a cross-sectional view of the vascular closure device of FIG. 1 taken along cross-section indicators 1B-1B.

The detachable sealing tip assembly 18 includes a filament 70 (also referred to herein as a suture) and a sealing tip 72. The filament 70 includes distal and proximal ends 80, 82. The filament may be connected to the sealing tip 72 using, for example, a knot 84 (see FIG. 1B).

The sealing tip 72 includes distal and proximal ends 74, 76, and an attachment portion 78. The attachment portion 78 may be positioned at the proximal end 76. The attachment portion 78 may be in the form of, for example, an eyelet, aperture, or protrusion that provides a structure for anchoring of the filament 70 to the sealing tip 72. The attachment portion 78 may be formed integrally with the sealing tip 72, or may be formed separately and attached to the sealing tip 72 in a separate attachment step.

Figure 13A:
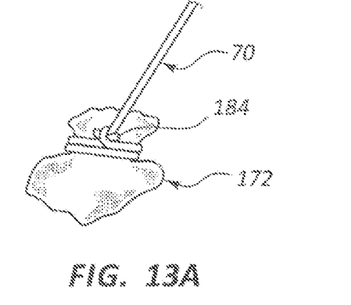
FIGS. 13A and 13B show another example detachable sealing tip for use with the vascular close device of FIG. 1.
Figure 13B:
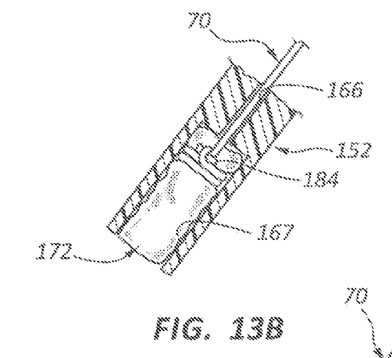

The sealing tip 72 may be in the form of a capsule having a generally circular cross-section with rounded surfaces at the distal and proximal ends 74, 76. Other constructions are possible for the sealing tip 72, such as those shown in FIGS. 13A-15. FIGS. 13A and 13B show a sealing tip 172 formed of a mesh material. The mesh material may have any desired shape and size. In one example, the mesh material has no particular shape. The filament 70 may be wrapped around an outer surface of the sealing tip 172 and secured with a knot 184. In other examples, the filament 70 may be secured to the sealing tip 172 using, for example, stitching, stapling or other attachment methods. The sealing tip 172 may be compacted and inserted within an inner tube 152 of a balloon location device. The inner tube 152 may include a lumen 166 and a sealing tip cavity 167. The filament 70 may extend through the lumen 166 and connected to the sealing tip 172, which is positioned within the sealing tip cavity 167. In some examples, the sealing tip 172 may be ejected out of the inner tube 152 using, for example, an election member such as a tube, which extends over the filament 70, through the lumen 166 and into contact with a proximal end surface of the sealing tip 172. In other examples, the sealing tip 172 automatically moves out of the sealing tip cavity 167 upon releasing tension in the filament 70.

Figure 14:
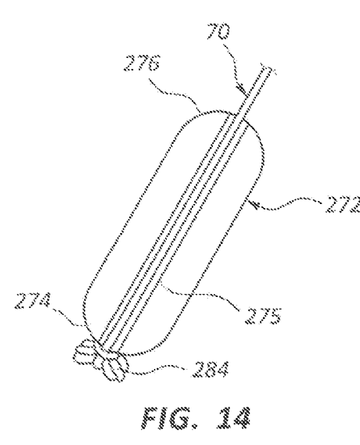
FIG. 14 shows another example detachable sealing tip for use with the vascular close device of FIG. 1.

FIG. 14 shows another embodiment of a sealing tip 272 having distal and proximal ends 274, 276 and a tip bore 275. In some examples, the sealing tip 272 has a construction similar to the sealing tip 72 but with the addition of tip bore 275. The filament 70 may extend through the tip bore 275 and be anchored at the distal end 274. A knot 284 may be formed in the filament 70 to provide the anchoring the distal end 274. In other examples, the filament 70 may be co-molded with the material of the distal end 274. Anchoring the filament 70 at the distal end 274 may result in at least some rotation force being applied to the sealing tip 272 if the sealing tip 272 attempts to move distally. This tendency of the sealing tip 272 to rotate upon moving distally may provide further resistance to distal motion.

Figure 15:
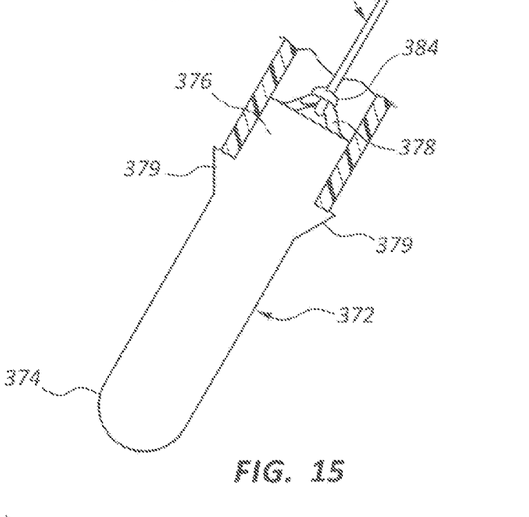
FIG. 15 shows another example detachable sealing tip for use with the vascular close device of FIG. 1.

FIG. 15 shows another example sealing tip 372 having distal and proximal ends 374, 376, an attachment point 378, and at least one barb member 379. The filament 70 is attached at the attachment point 378. The barb 379 may extend radially outward from the tube that carries the sealing tip 372. The barb 379 may contact (e.g., embed within) the channel in which the sealing tip 372 is positioned. The barb 379 may help remove the sealing tip 372 from the tube that carries the sealing tip 372 upon releasing tension in the filament 70.

FIG. 15 also shows a greater portion of the proximal end 376 positioned within the tube carrying the sealing tip 372 as compared to other examples shown herein. Extending a portion of the sealing tip 372 within the tube may help stabilize and maintain an axial orientation of the sealing tip 372 during delivery into the vessel and later positioning within the channel of the bioadhesive.

Other options are available for attaching the filament 70 to a sealing tip. In one example, a distal end portion of the filament 70 may be co-molded within the sealing tip. In another example, the filament 70 may be weaved through a plurality of holes formed in the sealing tip. As discussed above, the sealing tip may be formed into a solid structure such as the capsule-shaped structure of sealing tip 72. Alternatively, the sealing tip may comprise a deformable material such as, for example, the mesh material of sealing tip 172.

Figure 3:
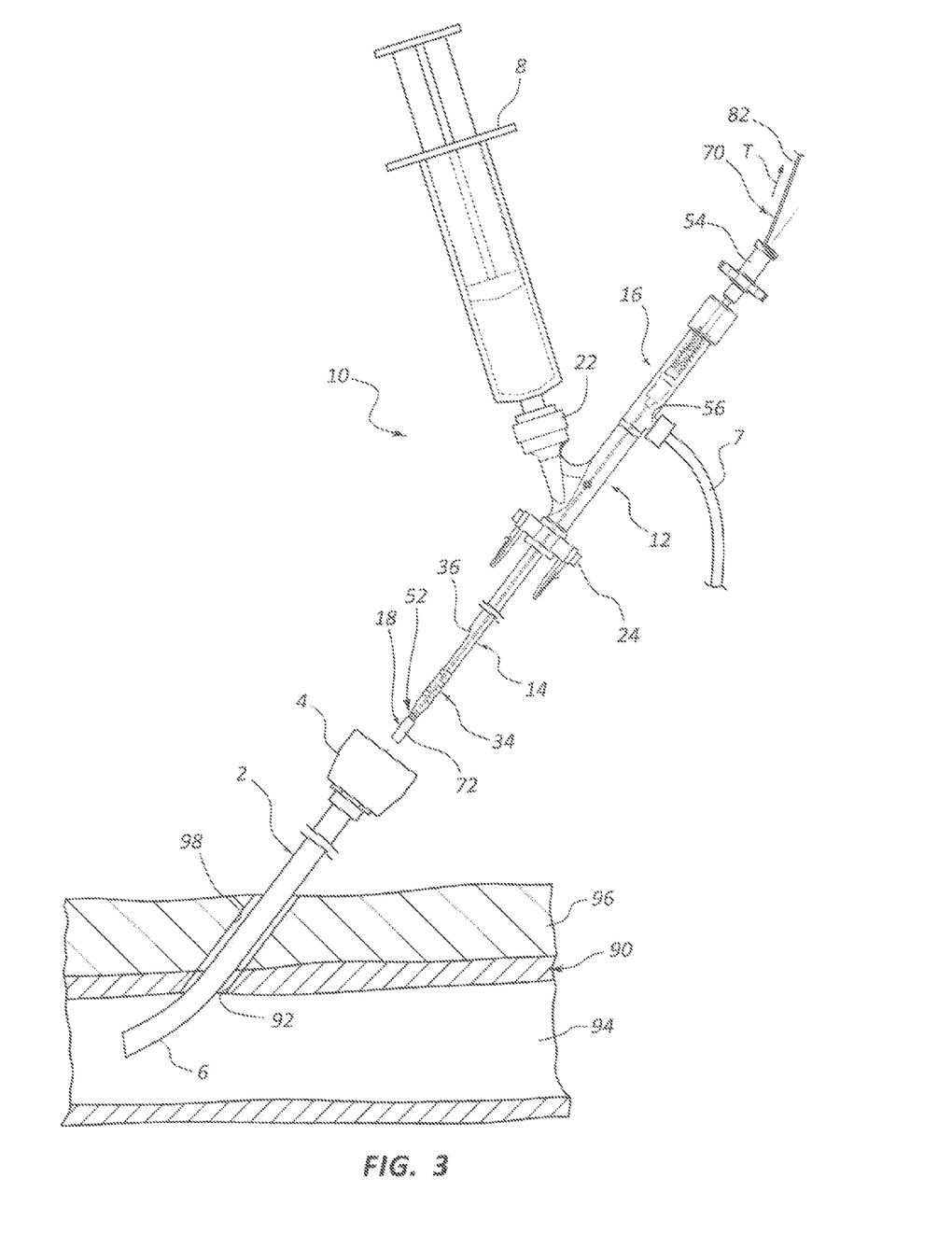
FIGS. 3-12 shows example method steps of sealing a vessel puncture using the vascular closure device of FIG. 1.

Referring now to FIGS. 3-11, an example method of sealing a vessel puncture using a vascular closure device 10 is shown and described. FIG. 3 shows a sheath 2 having a hub 4 and a distal end 6, which are advanced through a tissue tract 98 of a tissue layer 96, through a vessel puncture 92 of a vessel 90, and into a vessel lumen 94. The vascular closure device 10 is axially aligned with the hub 4. A first bioadhesive carrier 8 may be mounted to the injection port 22 of the manifold 12. An inflation fluid source 7 may be connected to the inflation manifold 56 of the balloon location device 16. The filament 70 may be arranged with the proximal end 82 extending proximally from the balloon location device 16. A tension force T may be applied to the filament 70 to maintain connection of the sealing tip 72 to the vascular closure device 10. The tension force T may be maintained, for example, by securing the distal end 80 of the filament 70 to a portion of the vascular closure device 10 such as, for example, the inner tube manifold 54, an actuator associated with one of the manifold 12 and housing 50, or a separate device that may be mounted to, for example, the inner tube manifold 54 at a proximal portion of the vascular closure device 10.

Figure 4:
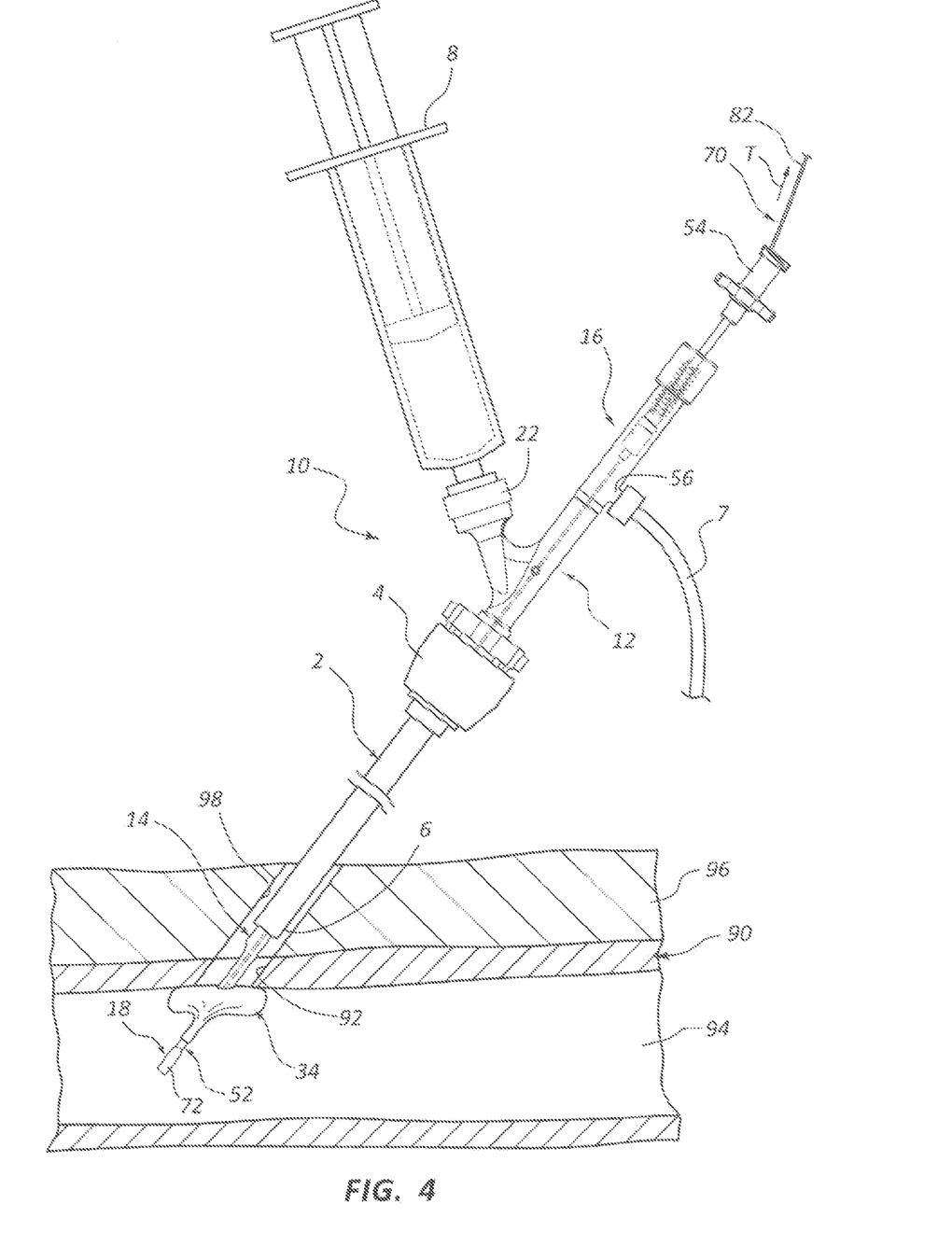

FIG. 4 shows the vascular closure device 10 advanced through the sheath 2 to position the balloon 34 and sealing tip 72 within the vessel lumen 94. A volume of inflation fluid is advanced from inflation fluid source 7 to the balloon 34 to inflate the balloon 34. The vascular closure device 10 and sheath 2 are withdrawn until the balloon 34 contacts an inner surface of the vessel 90 adjacent to the vessel puncture 92. The inflated balloon 34 provides temporary hemostasis through the vessel puncture 92.

Figure 5:
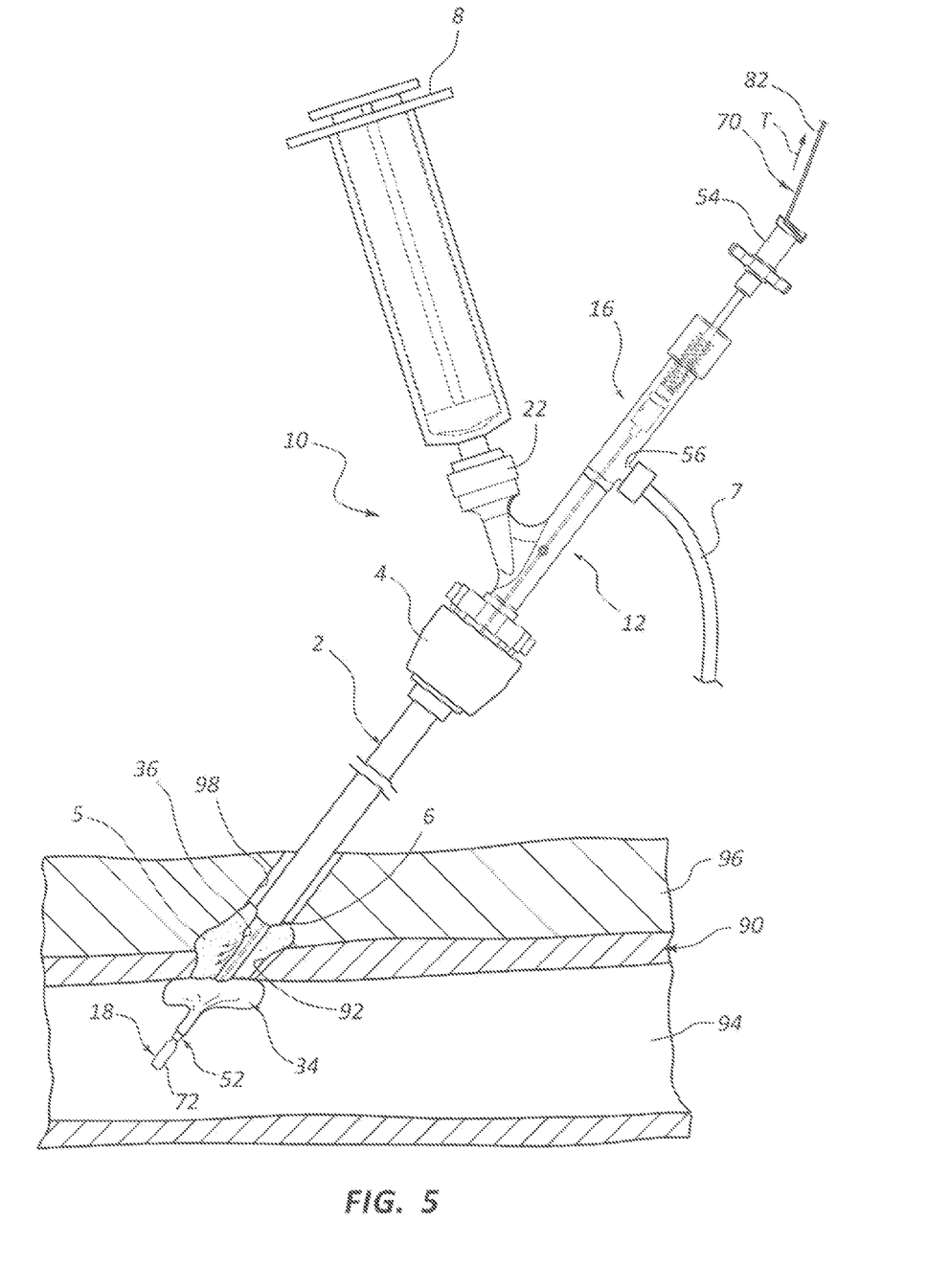

FIG. 5 shows a volume of bioadhesive advanced into the tissue tract 98 and vessel puncture 92. The volume of bioadhesive may be delivered by actuating the first bioadhesive carrier 8 (e.g., depressing a syringe plunger). The bioadhesive is elected out of the distal opening 36 of the delivery tube 14. The bioadhesive may form a first bioadhesive plug 5. The balloon 34 may limit movement of the first bioadhesive plug 5 through the vessel puncture 92 into the vessel lumen 94.

Figure 6:
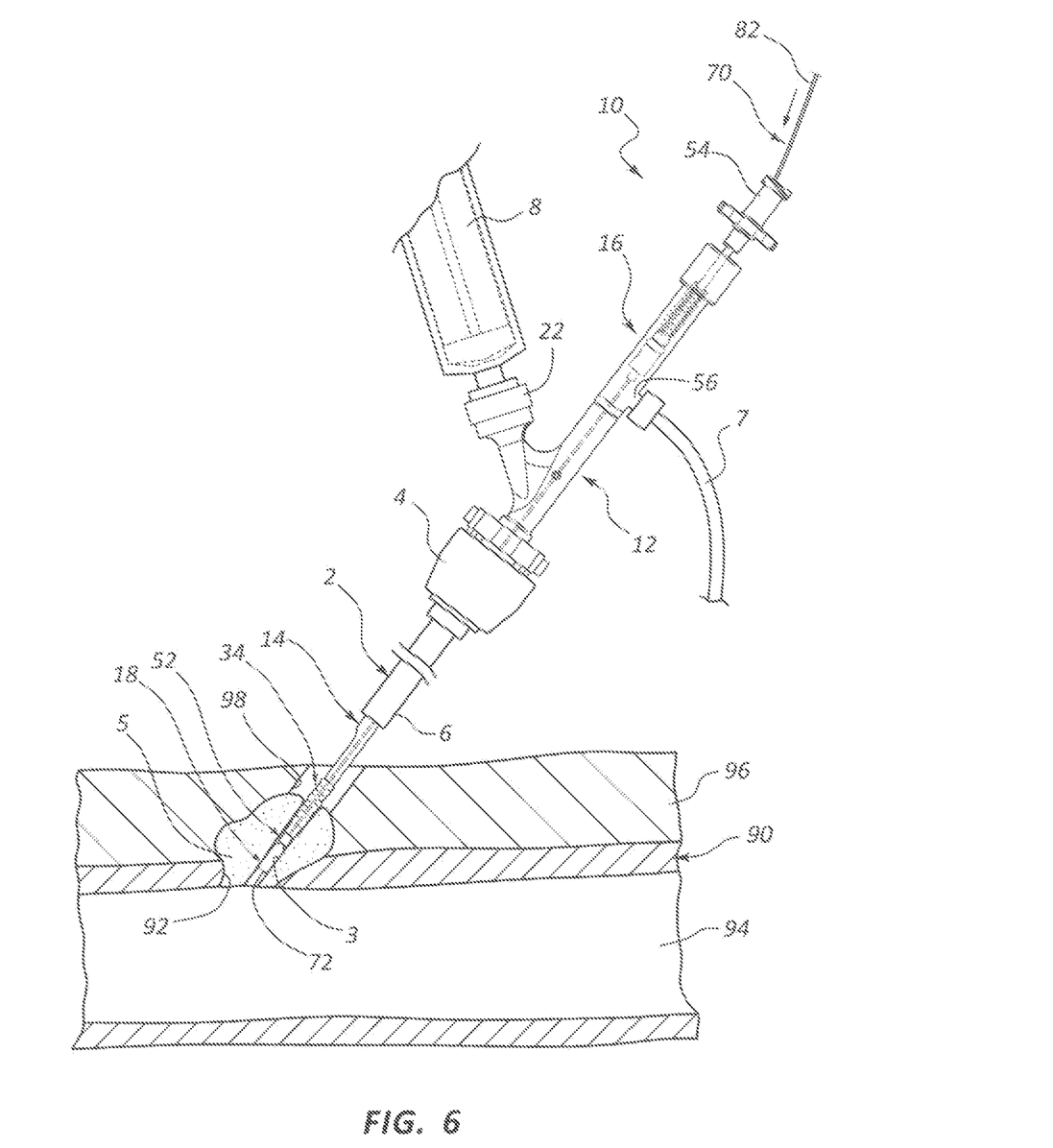

After the first bioadhesive plug 5 is at least partially cured (e.g., cured to the extent that the first bioadhesive plug 5 will not flow into the vessel lumen 94 upon deflation of the balloon 34), the balloon 34 is deflated and withdrawn through the first bioadhesive plug 5 as shown in FIG. 6. The vascular closure device 10 and sheath 2 are withdrawn a distance sufficient to position the detachable sealing tip 72 within a plug channel 3 in the first bioadhesive plug 5, which is formed upon withdrawing the vascular closure device 10 as shown in FIG. 6. At this point, the operator may release the tension force T in the filament 70 to release the sealing tip 72 from the balloon location device 16. The first bioadhesive plug 5 may maintain the sealing tip 72 lodged within the plug channel 3 based at least in part on, for example, the size and shape of the sealing tip 72 along with properties of the sealing tip 72. The sealing tip 72 may provide hemostasis through the plug channel 3 at least temporarily until further bioadhesive is delivered to the tissue tract 98 or the plug channel 3 collapses.

Figure 7:
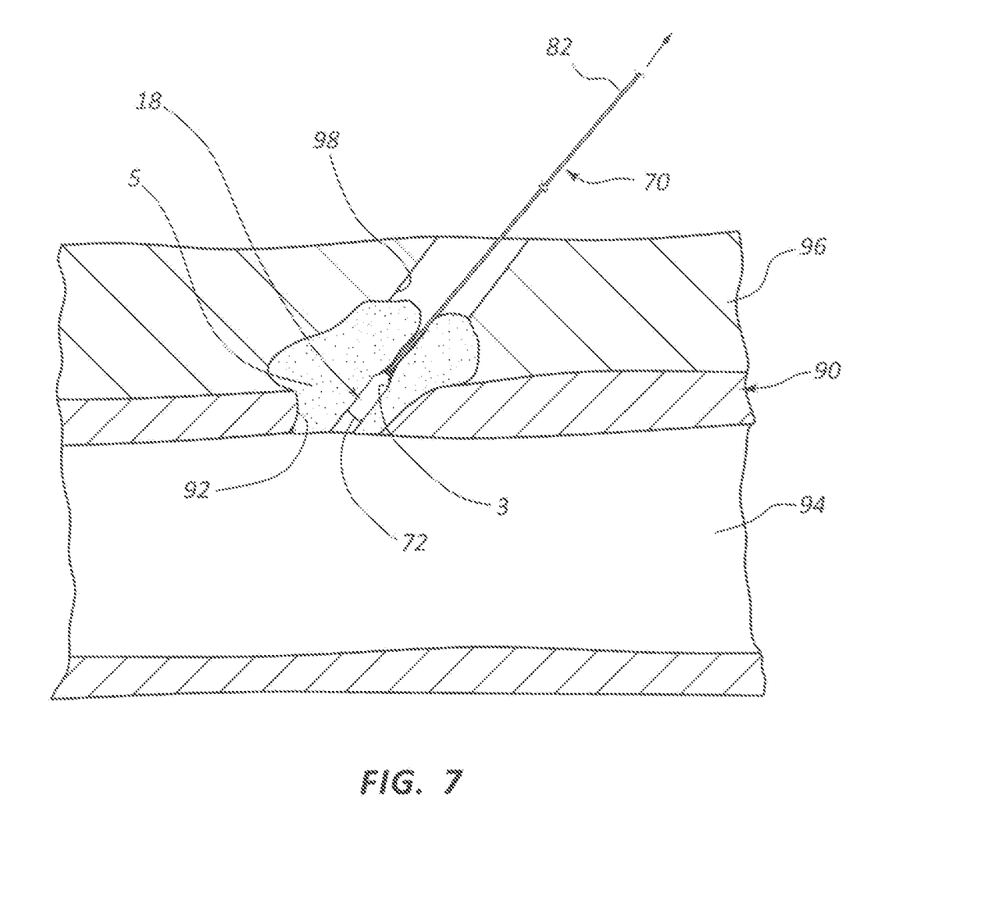

FIG. 7 shows the vascular closure device 10 and sheath 2 completely removed from the patient. The filament 70 extends through the tissue tract 98 to a location outside of the patient. The filament 70 may act as an anchor that helps hold the sealing tip 72 from moving distally into the vessel lumen 94. The filament 70 may be anchored by connection to the first bioadhesive plug 5. An optional retaining member may be used to secure the filament 70 outside of the patient to provide additional anchoring of the sealing tip 72.

Figure 8:
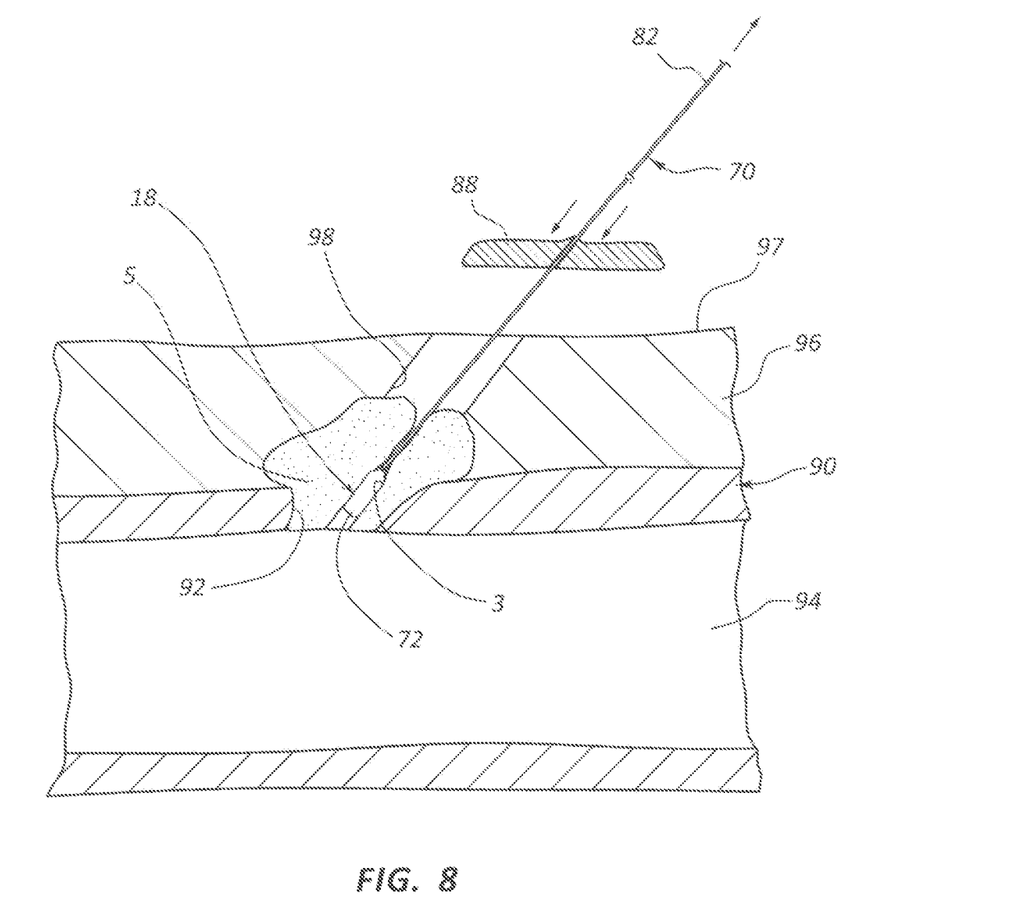
Figure 9:
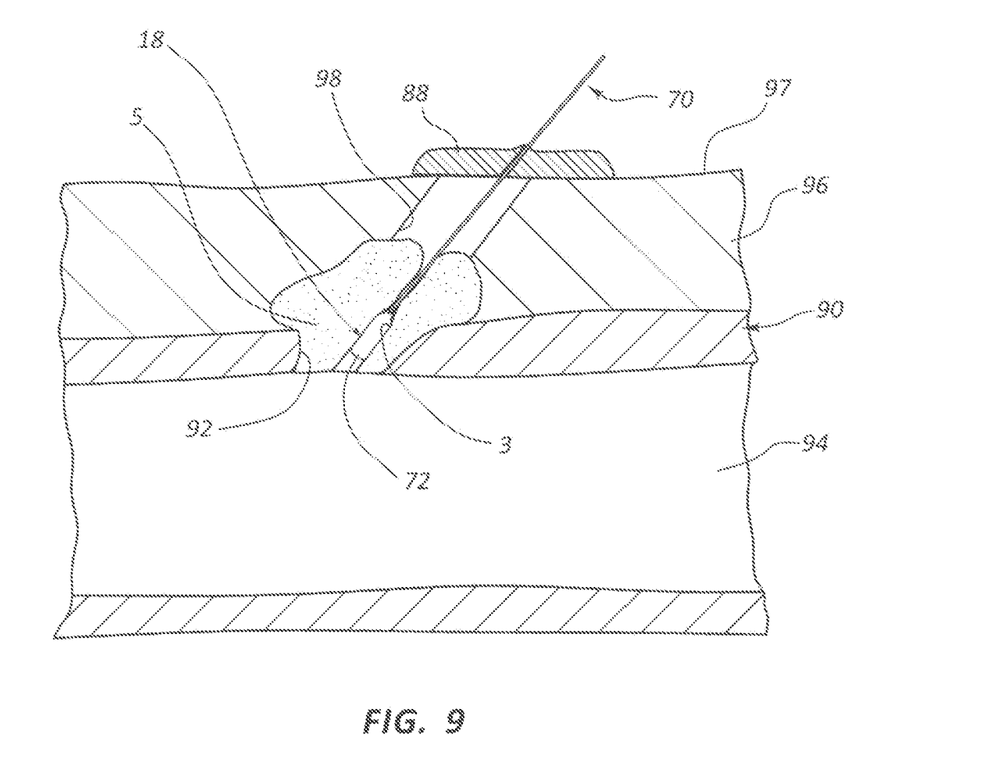

FIG. 8 shows a retaining member 88 being advanced along the filament 70. The retaining member 88 may have an opening that provides one-way passage of the filament 70 through the retaining member 88. The retaining member 88 contacts the outer skin surface 97 of the patient as shown in FIG. 9 to help maintain tension in the filament 70, which further anchors the sealing tip 72.

The retaining member 88 may be in the form of, for example, a disk. The disk may have a maximum width dimension (e.g., diameter) that is greater than the maximum width of the tissue tract 98 along the outer skin surface 97. The retaining member 88 may help distribute the tension forces in filament 70 across a greater surface area of the outer skin surface 97.

FIG. 10 shows an alternative or additional step for anchoring the filament 70 within the tissue tract 98. After depositing the sealing tip 72 within the plug channel 3, the vascular closure device 10 may be withdrawn to position the distal end 64 of the inner tube 52 proximal of the first bioadhesive plug 5 and within the tissue tract 98. A second volume of bioadhesive may be advanced through the inner tube 52. The second volume of bioadhesive may be supplied by a second bioadhesive carrier 8A. The second bioadhesive carrier 8A may be mounted to, for example, the inner tube manifold 54.

The second volume of bioadhesive material may encapsulate at least a portion of the filament 70 within the tissue tract 98. Upon curing, the second volume of bioadhesive may form a second bioadhesive plug 9. The second bioadhesive plug 9 may provide anchoring of filament 70 to help retain the sealing tip 72 in a fixed axial position within plug channel 3.

The second volume of bioadhesive may flow into the plug channel 3 proximal of the sealing tip 72. The second volume of bioadhesive may provide hemostasis of plug channel 3 and may also directly contact and connect to the sealing tip 72 within the plug channel 3.

Figure 11:
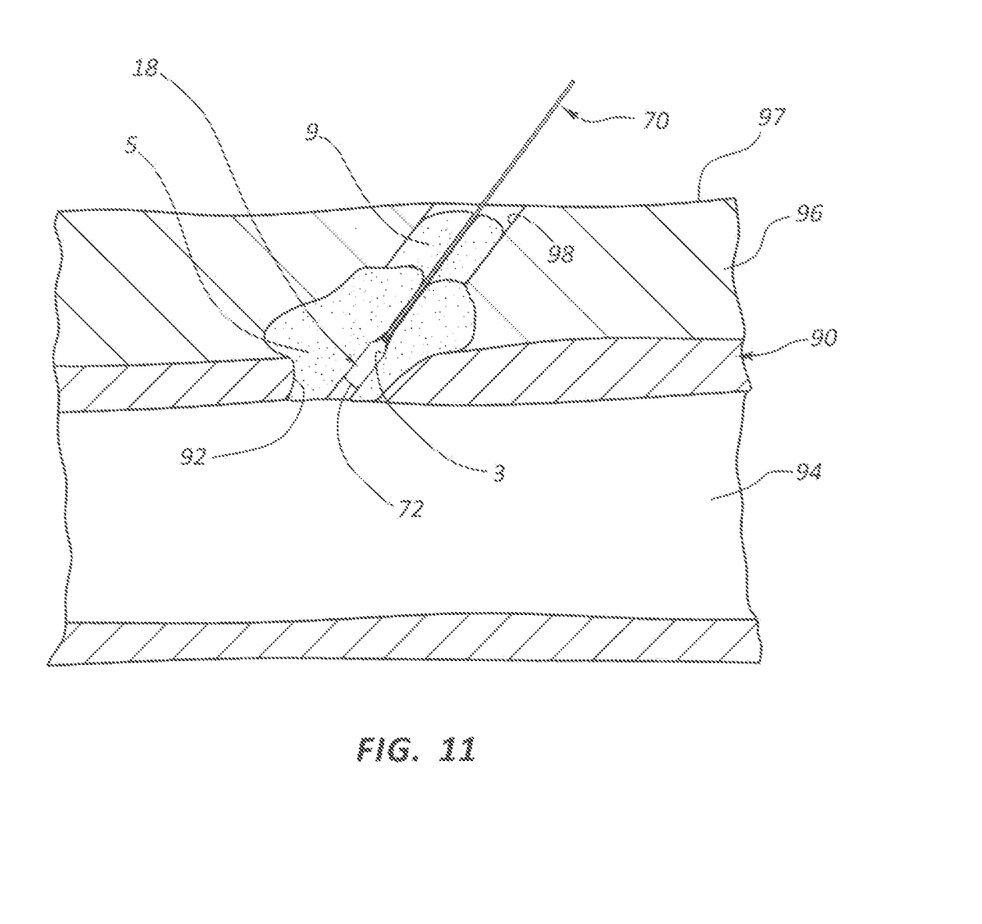
Figure 12:
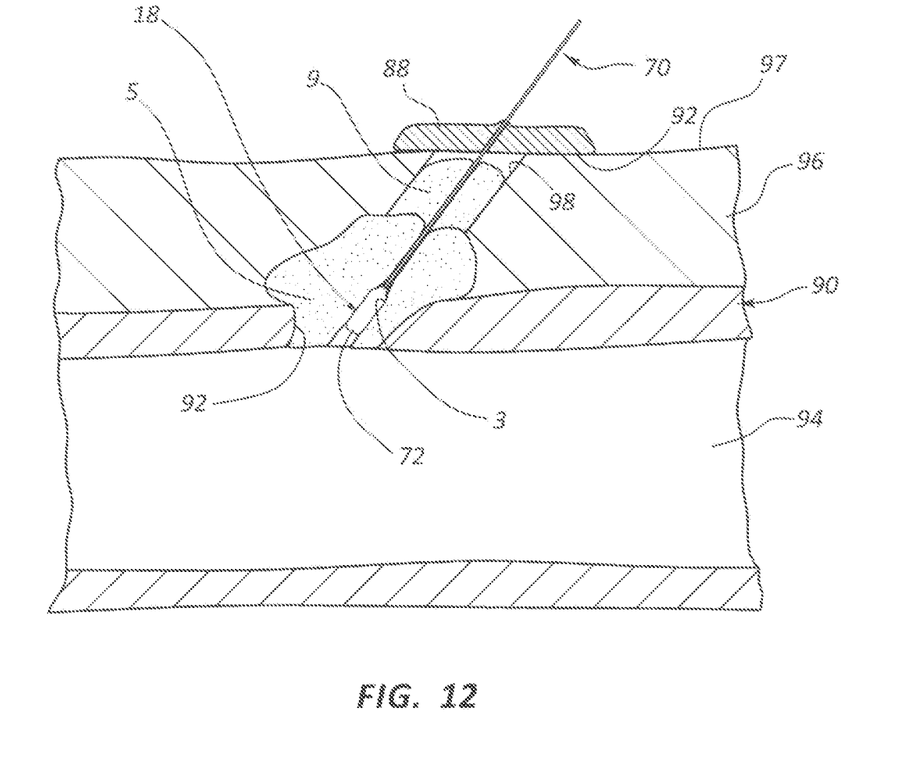

FIG. 11 shows the vascular closure device 10 removed, with the first and second bioadhesive plugs 5, 9 sealing the vessel puncture 92 and tissue tract 98 and providing an anchoring function for the filament 70. The filament 70 may be additionally anchored using an external retaining member such as retaining member 88 (see FIG. 12).

Figure 16:
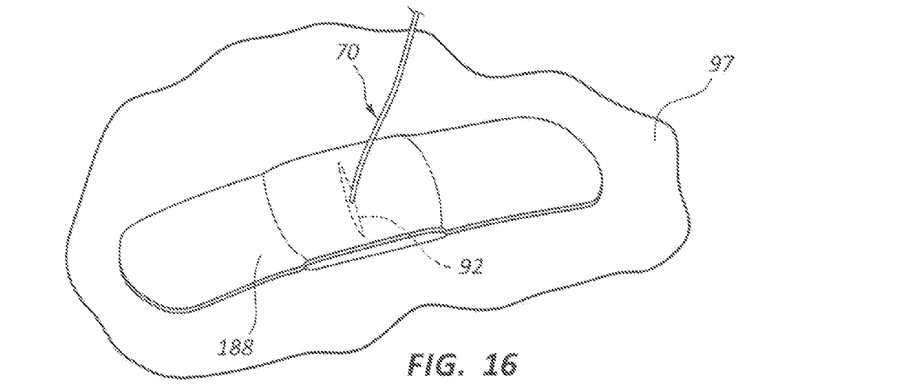
FIG. 16 shows an example retention member for securing a suture of the vascular close device of FIG. 1.

FIG. 16 shows an alternative retaining member 188. The retaining member 188 is in the form of a bandage or tape through which the filament 70 extends. The bandage may be secured to the filament 70 and may help hold the filament 70 from moving distally. The retaining member 188 may be secured directly to the skin surface. In at least some arrangements, at least a portion of the retaining member may extend through the skin surface.

As discussed above, the materials used for the first and second bioadhesive plugs 5, 9, the sealing tip 72, and filament 70 may be selected to maximize the anchoring effect of the filament 70. In one example, the materials of the filament 70 are resorbable at a slower rate than the materials of the sealing tip 72 and the first and second bioadhesive plugs 5, 9. In at least some examples, the sealing tip 72 comprises materials that are resorbable at a faster rate than the materials of the first and second bioadhesive plugs 5, 9.

Some example features and advantages related to the detachable sealing tip assemblies disclosed herein include, for example, providing a tethered detachable tip for adhesive-based extravascular closure devices having enhanced in vivo device safety and minimized device profile. The tethered suture may secure the bioresorbable tip in the adhesive channel to limit the possibility of emboli risk to the patient if the detachable tip were to slip into the vessel. The detachable tip is not required to have any specific geometry (e.g., outer diameter), which may provide the option of having a lower device profile and improved manufacturing processes. The materials for the sealing tip and suture may include existing FDA-approved materials for similar clinical use, thereby limiting regulatory barriers. The biodegration profiles of the detachable tip, suture and bioadhesive materials may be tunable in order to achieve improved safety and other objectives during resorption. The materials for the sealing tip (e.g., solid or mesh) may be designed and integrated with the vascular closure device for lower force, controlled tip release after the balloon is deflated and removed from the vessel. The tethered suture may be embedded within the second injection of bioadhesive upon curing to provide immediate anchoring of the detachable tip. The detachable tip may be further secured using an additional skin securement component as described above.

While this invention has been described with reference to certain specific embodiments and examples, it will be recognized by those skilled in the art that many variations are possible without departing from the scope and spirit of this invention. The invention, as defined by the chums, is intended to cover all changes and modifications of the invention which do not depart from the spirit of the invention.

What is claimed is:

1. A vascular closure device, comprising:
   a vessel locating device having an expandable portion configured to extend through and temporarily seal a vessel puncture from within a vessel, the vessel locating device having a distal end;
   a sealant delivery device configured to deliver a first volume of flowable sealant to the vessel puncture along an exterior of the vessel;
   a detachable sealing tip carried at a distal end of the vessel locating device, a first portion of the detachable sealing tip extending beyond the distal end of the vessel locating device, a second portion of the detachable sealing tip being inside of the distal end of the vessel locating device;
   a suture connected to and extending proximally from the detachable sealing tip;
   wherein the detachable sealing tip is configured for release within the first volume of flowable sealant upon withdrawal of the vessel locating device through the first volume of flowable sealant, the suture being anchored proximal of the detachable sealing tip.

2. The vascular closure device of claim 1, wherein the suture is connected to a distal end of the detachable sealing tip.

3. The vascular closure device of claim 1, wherein the suture is connected to a proximal end of the detachable sealing tip.

4. The vascular closure device of claim 1, wherein the detachable sealing tip has an elongate cylindrical shape.

5. The vascular closure device of claim 1, wherein the detachable sealing tip comprises a mesh material.

6. The vascular closure device of claim 1, wherein the suture wraps around the detachable sealing tip.

7. The vascular closure device of claim 1, wherein the suture is connected to a securement member, which contacts an outer skin surface.

8. The vascular closure device of claim 1, wherein the suture and detachable sealing tip each comprise a bioresorbable material, the bioresorbable material of the detachable sealing tip having a faster rate of resorption than a material of the suture.

9. The vascular closure device of claim 1, wherein the detachable sealing tip includes a lumen extending between distal and proximal ends of the detachable sealing tip, the suture extending through the lumen.

10. The vascular closure device of claim 1, wherein at least a portion of the detachable sealing tip is positioned within the vessel locating device prior to being detached within the first volume of flowable sealant.

11. The vascular closure device of claim 1, wherein the sealant delivery device comprises first and second lumens, the first volume of flowable sealant being delivered through the first lumen, and the vessel locating device extends through the second lumen.

12. The vascular closure device of claim 1, wherein the suture is encapsulated in a second volume of flowable sealant positioned proximal of the first volume of flowable sealant to anchor the suture.

13. A vascular closure device for sealing a vessel puncture of a patient, comprising:
   a sealant delivery device configured to deposit a volume of flowable sealant adjacent to a vessel puncture;
   a detachable sealing tip assembly configured to seal a channel formed in the volume of flowable sealant upon removal of the vascular closure device from the patient, the detachable sealing tip assembly comprising:
   a carrier tube;
   a sealing tip positioned at a distal end of the carrier tube, the sealing tip being at least partially inside the distal end and extending at least partially beyond the distal end upon insertion of the carrier tube into the vessel puncture;
   a suture having a distal end releasably connected to the sealing tip and a proximal end extending outside of the patient;
   a securement device connected to the proximal end of the suture and configured to anchor the sealing tip against an outer skin surface of the patient after the sealing tip is released from the carrier tube within the channel.

14. The vascular closure device of claim 13, wherein the suture fixes the sealing tip relative to the carrier tube until the sealing tip is released in the channel.

15. The vascular closure device of claim 13, wherein the securement device is connected to the suture after removal of the vascular closure device from the patient.

16. The vascular closure device of claim 13, further comprising an expandable balloon mounted to the carrier tube at a location proximal of the sealing tip, the expandable balloon being operable to temporarily seal the vessel puncture during delivery of the volume of flowable sealant.

* * * * *